(12) United States Patent
Anderton et al.

(10) Patent No.: US 7,974,381 B2
(45) Date of Patent: Jul. 5, 2011

(54) SYSTEMS, METHODS AND APPARATUS FOR A MOBILE IMAGING SYSTEM EQUIPPED WITH FUEL CELLS

(75) Inventors: Richard Larry Anderton, West Jordan, UT (US); Steven E. Curtis, Salt Lake City, UT (US)

(73) Assignee: General Electric Company, Schenectady, NY (US)

( * ) Notice: Subject to any disclaimer, the term of this patent is extended or adjusted under 35 U.S.C. 154(b) by 312 days.

(21) Appl. No.: 11/556,390

(22) Filed: Nov. 3, 2006

(65) Prior Publication Data
US 2008/0123814 A1    May 29, 2008

(51) Int. Cl.
*H05G 1/10* (2006.01)
(52) U.S. Cl. .................. 378/102; 378/101; 378/103
(58) Field of Classification Search .................. 378/101, 378/102, 103, 104, 105, 106, 107; 429/12
See application file for complete search history.

(56) References Cited

U.S. PATENT DOCUMENTS

| 5,401,589 | A | * | 3/1995 | Palmer et al. | 429/13 |
|---|---|---|---|---|---|
| RE35,025 | E |  | 8/1995 | Anderton |  |
| 5,976,722 | A | * | 11/1999 | Muller et al. | 429/13 |
| 6,169,782 | B1 | * | 1/2001 | Zetterlund | 378/103 |
| 6,787,259 | B2 | * | 9/2004 | Colborn et al. | 429/23 |
| 7,052,790 | B2 | * | 5/2006 | Nakamura et al. | 429/26 |
| 7,192,667 | B2 | * | 3/2007 | Yang et al. | 429/25 |
| 7,233,645 | B2 | * | 6/2007 | Feda | 378/102 |
| 7,239,113 | B2 | * | 7/2007 | Johnson | 322/58 |
| 7,479,338 | B2 | * | 1/2009 | Sato et al. | 429/24 |

\* cited by examiner

*Primary Examiner* — Allen C. Ho
(74) *Attorney, Agent, or Firm* — William Baxter, Esq.; Michael G. Smith, Esq.; Ellis Ramirez, Esq.

(57) ABSTRACT

Systems, methods and apparatus are provided through which in some embodiments, a mobile imaging system includes one or more fuel cells. Some embodiments include further electric power sources, such as battery and/or an external AC power source.

20 Claims, 6 Drawing Sheets

SYSTEMS, METHODS AND APPARATUS FOR A MOBILE IMAGING SYSTEM EQUIPPED WITH FUEL CELLS

FIELD OF THE INVENTION

This invention relates generally to imaging systems, and more particularly to power sources of mobile healthcare imaging systems.

BACKGROUND OF THE INVENTION

Conventional imaging systems receive power from one or more sources. The sources include batteries and an external alternating current (AC) power source coupled to electrical wall outlets. For many imaging systems, the primary source of power is the external AC power source coupled to electrical wall outlets.

However, certain functions of the imaging systems draw more power than can be supplied through the typical conventional electrical wall outlet. In particular, advanced mobile healthcare imaging systems may require more power than can be obtained from a conventional electrical wall outlet. For example, a mobile imaging system used for computed tomography (CT) or three-dimensional (3D) image reconstruction may need to energize motors for moving subsystems, provide power for the high voltage X-ray generation, provide active cooling for heat dissipation of the X-ray acquisition subsystem, power all other image processing and display subsystems, power interface and archiving devices, etc.

In the United States, AC power available at electrical wall outlets is conventionally limited to 15 amps and 115 volts. Standards from the International Electrotechnical Committee (IEC) located in Geneva Switzerland and other standards and regulations further limit the current from 15 amps to 12 amps, or 13.2 amps in the case of X-ray equipment. Alternate electrical wall outlets located in some facilities will allow up to 17.6 amps. Thus, the power that can be drawn from a 115 volt outlet can vary from 1400 to 2000 watts (the product of voltage and current), which is lower than is needed by the imaging system during operations discussed above.

In some conventional imaging systems, rechargeable battery pack(s) are used to augment power from the electrical wall outlet. The battery pack(s) provide intermittent short-term power when the imaging system requires more electrical power than the electrical wall outlet can supply. The batteries are recharged between high power events. This method is effective as long as the long-term average power draw from the battery charger and other electronic devices in the imaging system is below the electrical wall outlet power level that is allowed. Note also that separate electrical wall outlets in close proximity to each other may typically be wired on the same circuit, and so ampacity remains a concern.

For the reasons stated above, and for other reasons stated below which will become apparent to those skilled in the art upon reading and understanding the present specification, there is a need in the art for a power source to an imaging system that draws less power on average from a conventional electrical wall outlet power source including the power draw of electronic devices in the imaging system than the amount of power that can be supplied by the conventional power source supplied to an electrical wall outlet.

BRIEF DESCRIPTION OF THE INVENTION

The above-mentioned shortcomings, disadvantages and problems are addressed herein, which will be understood by reading and studying the following specification.

In one aspect, one or more fuel cell(s) augments the electrical power obtained from a wall outlet for mobile healthcare imaging equipment.

In another aspect, an apparatus to image objects includes an imaging system and one or more fuel cell electric power source(s) operably coupled to the imaging system. In some embodiments, the fuel cell electric power source(s) is operable to produce about 5 kW electrical output.

In yet another aspect, a mobile digital X-ray imaging system includes a power management system, at least one fuel cell electric power source operably coupled to the power management system through a control line, a high voltage inverter operably coupled to the at least one fuel cell electric power source through a power line and operably coupled to the power management system through a control line and an X-ray source operably coupled to the high voltage inverter through a power line.

In still another aspect, a method to control power in a mobile digital X-ray imaging system includes controlling power from at least one power module to a high voltage inverter, through at least one control line and controlling power from a fuel cell to the high voltage inverter through at least one control line.

Apparatus, systems, and methods of varying scope are described herein. In addition to the aspects and advantages described in this summary, further aspects and advantages will become apparent by reference to the drawings and by reading the detailed description that follows.

BRIEF DESCRIPTION OF THE DRAWINGS

FIG. 5 is a side view of mobile imaging system according to an embodiment that includes a fuel cell; and.

DETAILED DESCRIPTION OF THE INVENTION

In the following detailed description, reference is made to the accompanying drawings that form a part hereof, and in which is shown by way of illustration specific embodiments which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

The detailed description is divided into four sections. In the first section, a system level overview is described. In the second section, apparatus embodiments are described. In the third section, method embodiments are described. Finally, in the fourth section, a conclusion of the detailed description is provided.

System Level Overview

Figure 1:
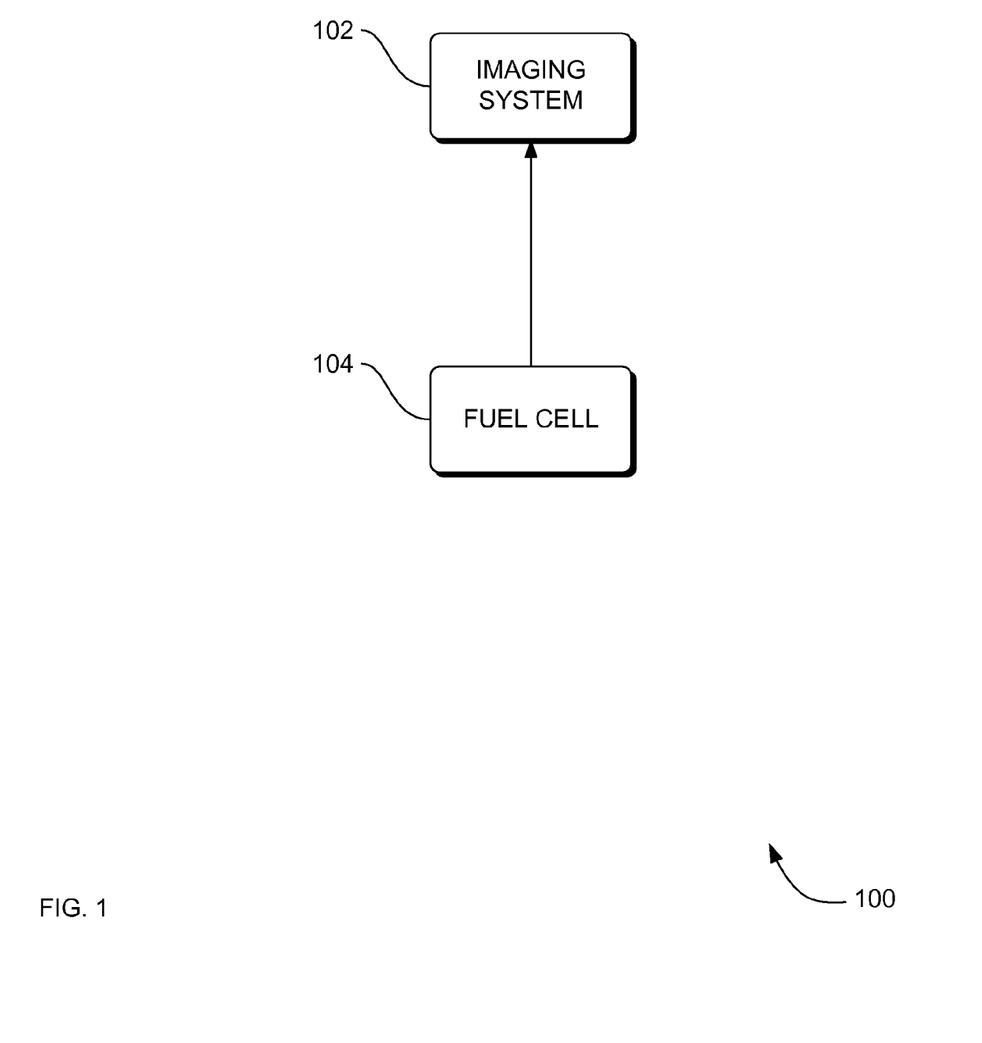
FIG. 1 is a block diagram of an overview of a system to image objects, according to an embodiment that includes a fuel cell.

FIG. 1 is a block diagram of an overview of a system 100 to image objects, according to an embodiment that includes a fuel cell. System 100 solves the need in the art for a power source to an imaging system that draws less power on average from a power draw of electronic devices in the imaging system than the amount of power that can be supplied by the conventional electrical wall outlet.

System 100 includes an imaging system 102 and one or more fuel cell power source(s) 104 that are operably coupled to the imaging system 102 to augment electrical power to the imaging system. Conventional fuel cell(s) 104 are electrochemical energy conversion devices that convert hydrogen and oxygen into water, and in the process, also produce electricity. Some, if not all of the electricity flows to imaging system 102. The fuel cell produces electricity as long as hydrogen and oxygen flow at sufficient levels from an external source. To create enough total voltage, the cells are layered and combined in series and parallel circuits to form a fuel cell stack. The number of cells used is dependent upon the power needed and varies with the particular design.

One example of a fuel cell power source 104 is a proton exchange membrane fuel cell (PEMFC) fuel cell (not shown). In a PEMFC fuel cell, pressurized hydrogen gas ($H_2$) enters the PEMFC fuel cell on an anode side and is forced through a catalyst by the pressure. When each $H_2$ molecules contact platinum on the catalyst, the molecule splits into two $H^+$ ions and two electrons ($e^-$). The electrons are conducted through the anode which is in turn operably coupled to the imaging system 102. On a cathode side of the PEMFC fuel cell, oxygen gas ($O_2$) is forced through the catalyst, where the $O_2$ forms two oxygen atoms. Each of the $O_2$ atoms has a strong negative charge. This negative charge attracts the two $H^+$ ions through the membrane, where the $H^+$ ion combines with an oxygen atom and two of the electrons from the external circuit to form a water molecule ($H_2O$). The $H_2O$ is waste or exhaust matter.

Other examples of a fuel cell power source 104 include electro-galvanic fuel cell, alkaline fuel cell, direct borohydride fuel cell, direct carbon fuel cell, direct-ethanol fuel cell, direct-methanol fuel cell, formic acid fuel cell, metal Hydride fuel cell, microbial fuel cell, molten-carbonate fuel cell, phosphoric-acid fuel cell, proton exchange membrane fuel cell, protonic ceramic fuel cell, reformed-methanol fuel cell, reversible fuel cell, flow fuel cells such as a reduction-oxidation (redox) fuel cell, solid-oxide fuel cell, and a zinc-air fuel cell.

In addition to $H_2$ fuel, other possible fuels include diesel, methanol (direct-methanol fuel cells) and chemical hydrides. The waste product from these other fuels is carbon dioxide, and water or water vapor, which can be exhausted from system 100 into the atmosphere.

Because the fuel cell(s) 104 does not use an external power source or a battery, the supply of electrical power to the imaging system 102 by the fuel cell(s) 104 solves the need in the art for a power source to an imaging system that draws less power on average from a conventional electrical wall outlet including the power draw of electronic devices in the imaging system than the amount of power that can be supplied by the conventional electrical wall outlet While the system 100 is not limited to any particular imaging system 102 or fuel cell(s) 104, but for sake of clarity, a simplified imaging system and fuel cell(s) are described.

Apparatus Embodiments

In the previous section, a system level overview of the operation of an embodiment was described. In this section, the particular apparatus of such an embodiment are described by reference to a series of diagrams.

Figure 2:
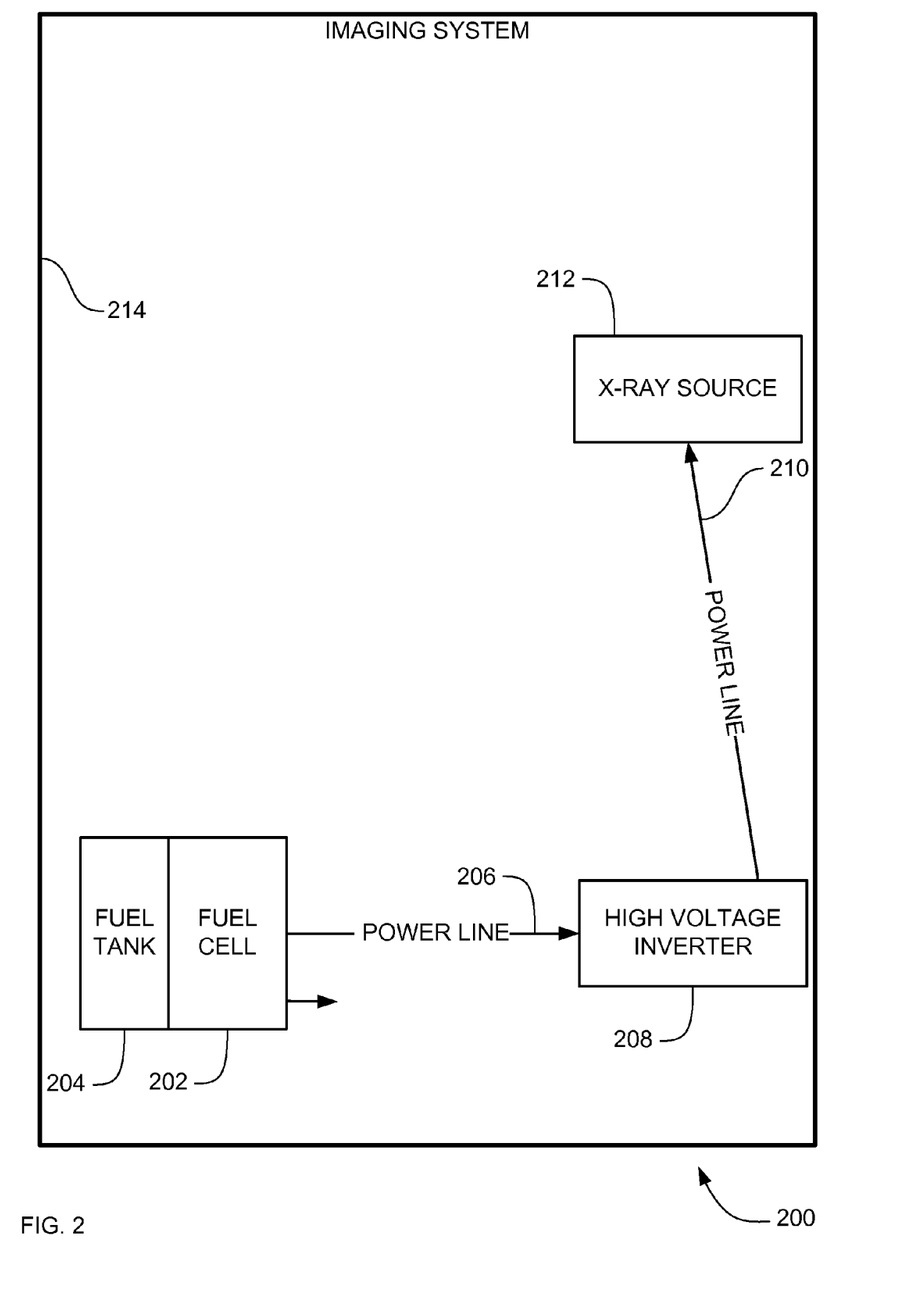
FIG. 2 is a block diagram of apparatus to image objects, according to an embodiment that includes a fuel cell and other apparatus.

FIG. 2 is a block diagram of apparatus 200 to image objects, according to an embodiment that includes a fuel cell, a fuel tank, a high voltage inverter, an X-ray source and other apparatus. Apparatus 200 is one embodiment of system 100 that is described above. Apparatus 200 solves the need in the art for a power source to an imaging system that draws less power on average from a power draw of electronic devices in the imaging system than the amount of power that can be supplied by a conventional electrical wall outlet.

Some embodiments of apparatus 200 include a fuel cell power source 202 that is operable to produce a required amount of power, such as about 5 kilo-watts (kW) of electrical power. Fuel cell 202 is one embodiment of fuel cell 104 in FIG. 1 above. Fuel cells are commercially available having anywhere from 25 W of electrical output which are often used to power personal computers, up to 70 kW of electrical output which are used to power automobiles.

In an embodiment, the fuel cell 202 produces electricity as long as a fuel such as hydrogen, and oxygen flow to the fuel cell 202 in a sufficient volume from an external source, such as a fuel tank 204. As discussed in greater detail below, fuel tanks for a 5 kW fuel cell 202 typically range in size from 1 gallon to 3 gallons, with 2.5 gallons being a size that provides an optimal balance between the amount of power that is generated by a 5 kW fuel cell 202 from 2.5 gallons of fuel such as hydrogen and a fuel tank 204 size that fits well within an imaging system, such as healthcare mobile X-ray imaging system 600 below.

Electricity that is produced by the fuel cell 202 is conducted through power line 206 which operably couples the fuel cell 202 to a high-voltage inverter 208. In some embodiments, the high-voltage inverter receives direct current (DC) power, converts the DC power to alternating current (AC) power, rectifies the AC power, and then converts the rectified AC power to DC power. The inverted power is conducted through power line 210 which operably couples the high-voltage inverter 208 to an X-ray source 212 for the high voltage X-ray generation, and other components of the imaging system, such as motors for moving subsystems, active cooling for heat dissipation of the X-ray generation and acquisition subsystems, all other image processing and display subsystems, power interface and data archiving devices, etc.

In some embodiments, the high-voltage inverter 208 may require an input DC power bus of, 200 VDC at 25 amps, for example, yielding 5 kW power delivery for intermittent time periods of peak power. Given the intermittent nature of this peak power need, the power can equivalent to about 1 kW average power delivery for a 4 hour time period per day, or 14.4 MJ of energy.

In some embodiments of apparatus 200, the fuel cell 202 is contained within a housing 214 of the apparatus 200.

The size, position and distance of the fuel cell 202, the fuel tank 204, power line 206, high voltage inverter 208, power line 210, X-ray source 212 and housing 214 shown in FIG. 2 are exemplary not necessarily reflective of actual configuration.

Based on requirements of the high-voltage inverter 208 and the X-ray source 212, required properties of the fuel tank 204 can be estimated or determined in some embodiment required for 1 day of usage. Depending on the type of fuel cell, conventional technology provides for the use of either a liquefied hydrocarbon (e.g., methanol), or hydrogen as the fuel. Hydrocarbons are easier to store and deposit into a tank (with under 20 atmospheres of pressure), but the hydrocarbon produces carbon dioxide, and water or water vapor, and possibly a small amount of other undesirable exhaust products. Assuming fuel cell inefficiencies and other considerations, a 1 gallon fuel tank could provide approximately 14.4 MJ of energy, as shown above to be required. Gaseous hydrogen produces only water as an exhaust, but is more difficult to deposit into a fuel cell tank, and must be stored under much higher pressure (perhaps 200 atmospheres) to obtain a reasonable tank size. Accounting for various considerations, a 2.5 gallon hydrogen fuel tank can provide the needed 14.4 MJ of energy in some embodiments.

While the apparatus 200 is not limited to any particular fuel cell 202, fuel tank 204, power line 206, high voltage inverter 208, power line 210, X-ray source 212 and housing 214, but for sake of clarity, a simplified fuel cell 202, fuel tank 204, power line 206, high voltage inverter 208, power line 210, X-ray source 212 and housing 214 are described.

Figure 3:
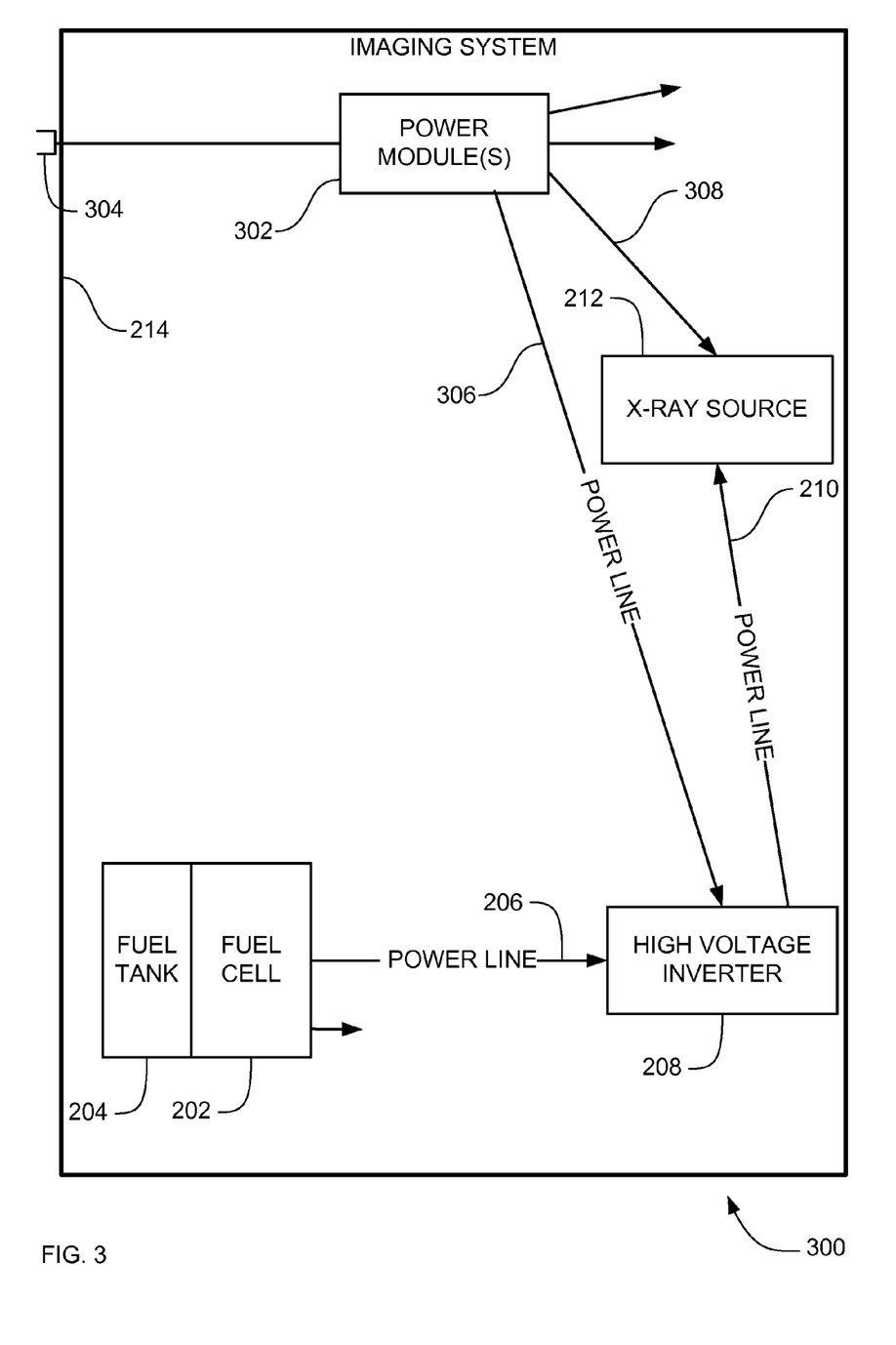
FIG. 3 is a block diagram of apparatus to image objects, according to an embodiment that includes a fuel cell, power module(s) and other apparatus.

FIG. 3 is a block diagram of apparatus 300 to image objects, according to an embodiment that includes a fuel cell, power module(s) and other apparatus. Apparatus 300 is one embodiment of system 100 that is described above. Apparatus 300 is one embodiment of apparatus 200 that is described above. Apparatus 200 solves the need in the art for a power source to an imaging system that draws less power on average from a power draw of electronic devices in the imaging system than the amount of power that can be supplied by a conventional electrical wall outlet.

Some embodiments of apparatus 300 include one or more power module(s) 302 that are operably coupled to the high voltage inverter 208. The power module(s) are also operable to be electrically and mechanically coupled to an electrical wall outlet 304. In some embodiments, the power modules(s) 302 include one or more batteries.

Some embodiments of apparatus 300 also include a power line 306. Electricity from power module(s) 302 is conducted through power line 306 which operably couples the power module(s) 302 to the high-voltage inverter 208.

Some embodiments of apparatus 300 also include a power line 308. Electricity from power module(s) 302 is conducted through power line 308 which operably couples the power module(s) 302 to the X-ray source 212.

The waste or exhaust matter of the fuel cell 202 may be collected in an exhaust receptacle 310, from which the waste is disposed. For example, $H_2O$ waste of a hydrogen fuel cell may be collected in an exhaust water pan, from which the $H_2O$ waste is disposed.

Figure 4:
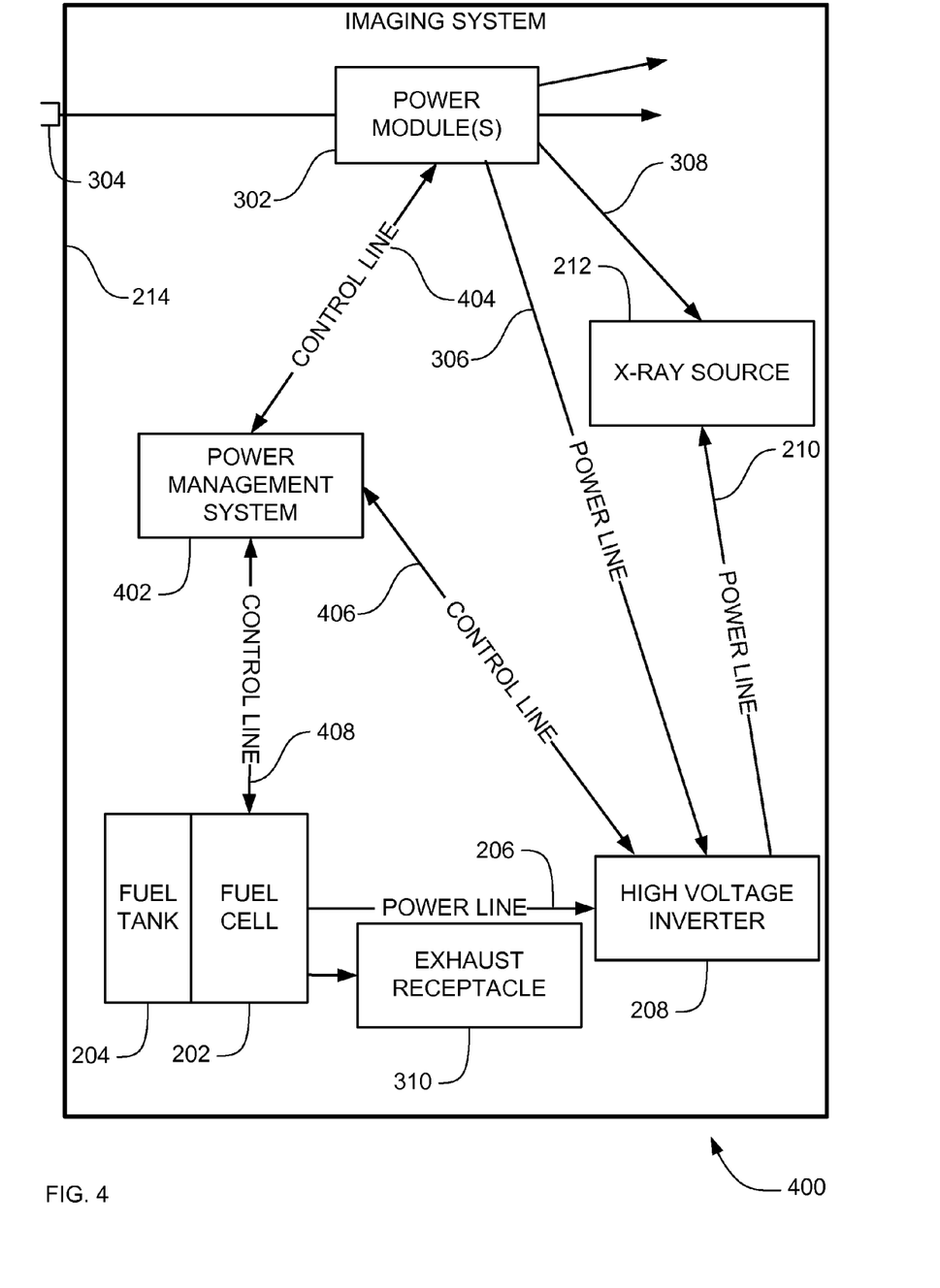
FIG. 4 is a block diagram of apparatus to image objects, according to an embodiment that includes a fuel cell, power module(s), a power management system and other apparatus.

FIG. 4 is a block diagram of apparatus 400 to image objects, according to an embodiment that includes a fuel cell, a power management system and other apparatus. Apparatus 400 is one embodiment of system 100 that is described above. Apparatus 400 is one embodiment of apparatus 200 that is described above. Apparatus 400 is one embodiment of apparatus 300 that is described above. Apparatus 300 solves the need in the art for a power source to an imaging system that draws less power on average from a power draw of electronic devices in the imaging system than the amount of power that can be supplied by a conventional electrical wall outlet.

Apparatus 400 includes a power management system 402. In some embodiments, the power management system 402 is operable to control power from the power module(s) 302 to the high voltage inverter 208 through one or more control lines 404 and/or 406. In which case, the power management system 402 is operably coupled to the high voltage inverter 208 and operably coupled to the power module(s) 302.

In some embodiments, the power management system 402 is operable to control power from the fuel cell 202 to the high voltage inverter through one or more control lines 406 and/or 408. In which case, the power management system 402 is operably coupled to the high voltage inverter 208 and operably coupled to the at least one fuel cell 202.

Figure 5:
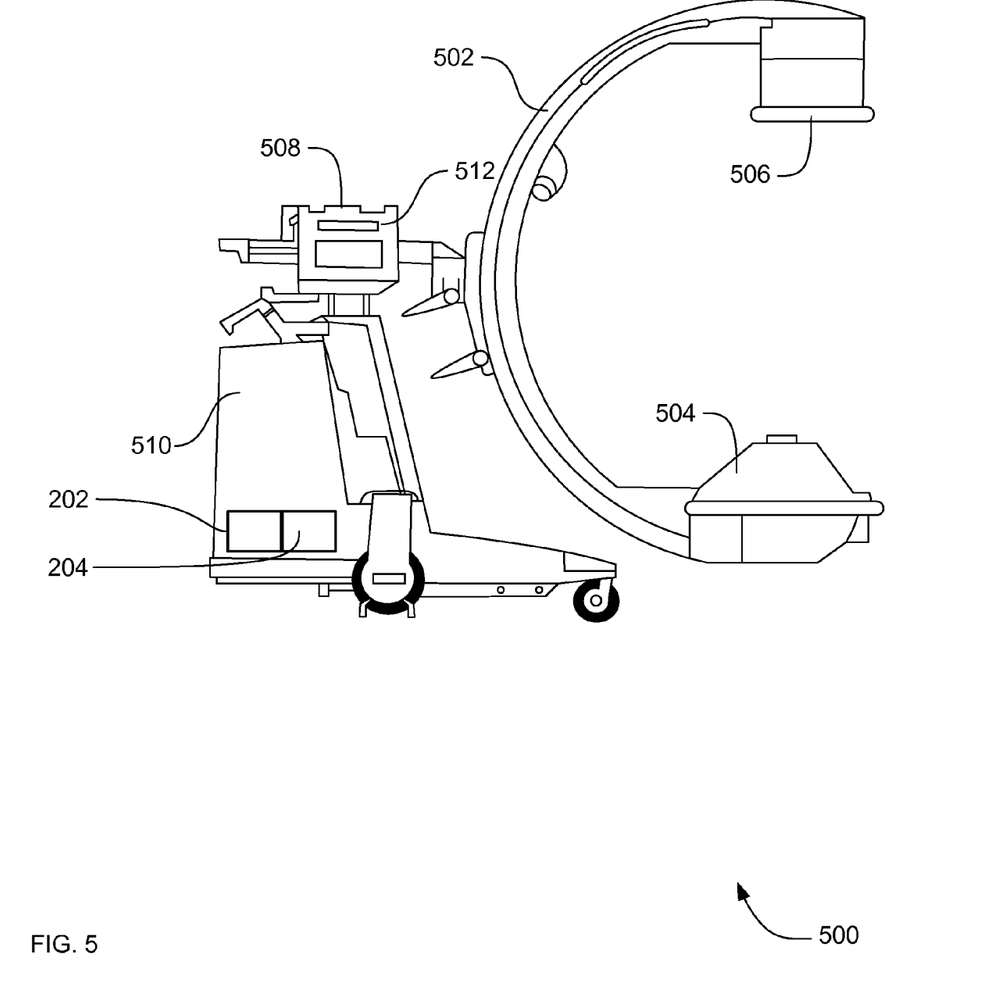

FIG. 5 is a side view of mobile X-ray imaging system 500 according to an embodiment having a fuel cell and a fuel tank. Apparatus 500 solves the need in the art for a power source to an imaging system that draws less power on average from a power draw of electronic devices in the imaging system than the amount of power that can be supplied by the conventional electrical wall outlet.

System 500 generally includes a gantry 502 having an X-ray source 504 at one end of the gantry 502 and an image receptor 506 at the opposite end of the gantry 502. The gantry 502 is pivotably mounted to a support structure 508 that contains a motion controller 512 that provides powered motion to move the gantry into position for imaging. The support structure 508 is mounted on a wheeled base 510 that allows the system 500 to be moved from place to place.

Mobile X-ray imaging system 500 also includes a fuel cell, such as fuel cell 104 or 202. In addition, mobile X-ray imaging system 500 includes a fuel tank, such as fuel tank 204. Other embodiments of mobile X-ray imaging system 500 include other components disclosed in FIG. 1, FIG. 2, FIG. 3, FIG. 4, and FIG. 5. Systems other than the mobile X-ray imaging system 500 than can include components disclosed in FIG. 1, FIG. 2, FIG. 3, FIG. 4, and FIG. 5 include a mobile imaging system, a mobile healthcare imaging system, and a mobile healthcare X-ray imaging system.

Method Embodiments

In the previous section, apparatus of the operation of an embodiment was described. In this section, the particular methods that can performed by a computer, processor, or microprocessor environment and are described by reference to a series of flowcharts.

Figure 6:
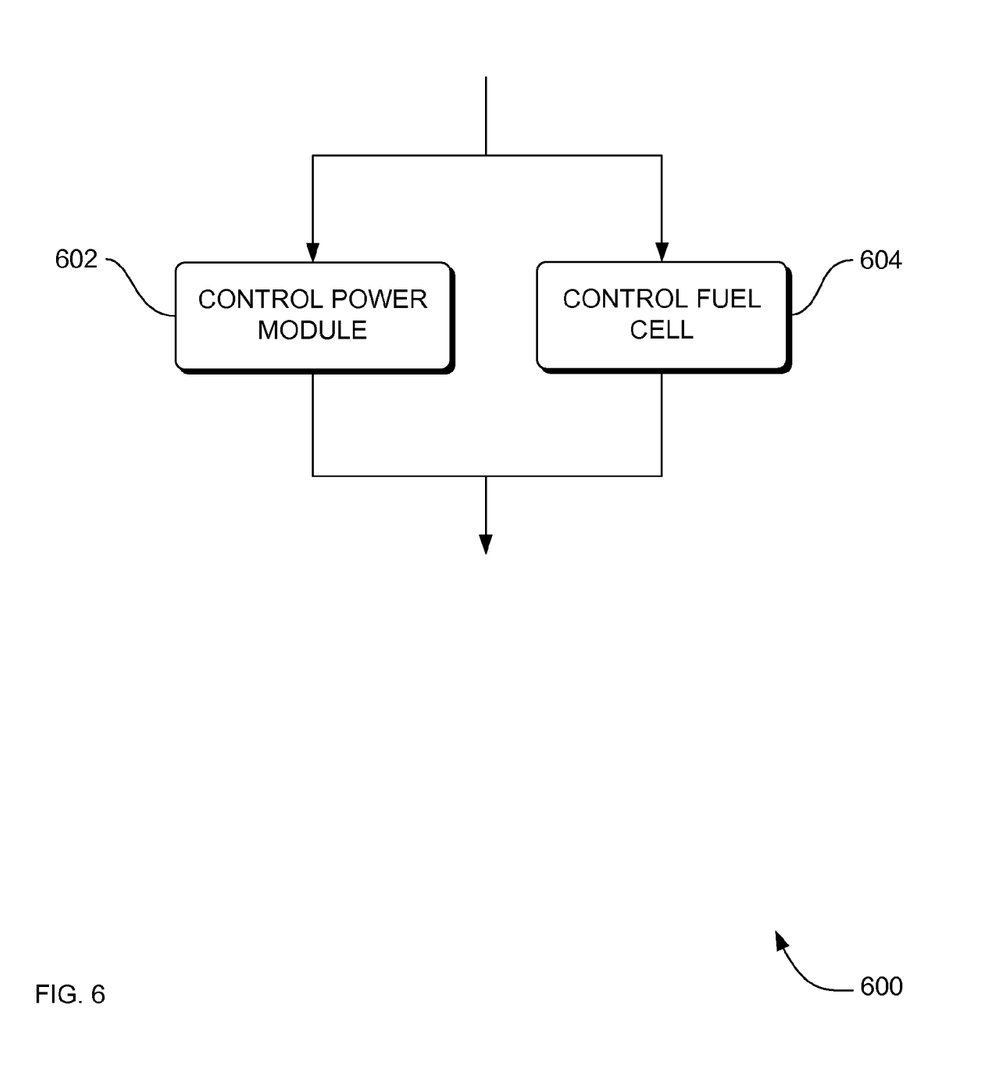
FIG. 6 is a flowchart of a method to control power in a mobile imaging system, according to an embodiment.

FIG. 6 is a flowchart of a method 600 to control power in a mobile imaging system, according to an embodiment. Method 600 solves the need in the art for a power source to an imaging system that draws less power on average from a power draw of electronic devices in the imaging system than the amount of power that can be supplied by a conventional electrical wall outlet.

Method 600 includes controlling 602 power from at least one power module, such as power module(s) 302, to a high voltage inverter, through at least one control line such as control line 404. Method 600 also includes controlling 604 power from a fuel cell, such as fuel cell 104 or 202 to the high voltage inverter through at least one control line, such as control line 408. The controlling actions 602 and 604 can be performed in any order relative to each other and/or the actions 602 and 604 can be performed simultaneously.

In some embodiments, method 600 is implemented as a computer data signal embodied in a carrier wave, that represents a sequence of instructions which, when executed by a processor cause the processor to perform the respective method. In other embodiments, method 600 is implemented as a computer-accessible medium having executable instructions capable of directing a processor to perform the respective method. In varying embodiments, the medium is a magnetic medium, an electronic medium, or an optical medium.

Embodiments are described in terms of a computer executing computer-executable instructions. However, some embodiments can be implemented entirely in computer hardware in which the computer-executable instructions are implemented in read-only memory. Some embodiments can also be implemented in client/server computing environments where remote devices that perform tasks are linked through a communications network. Program modules can be located in both local and remote memory storage devices in a distributed computing environment.

CONCLUSION

An imaging system having a fuel cell power supply is described herein.

Advanced mobile healthcare imaging systems often require more power than can be obtained from a typical electrical wall outlet receptacle. For example, a mobile imaging system used for computed tomography (CT) or three-dimensional (3D) image reconstruction may need a high amount of power for a short period of time. In order to provide adequate power for these advanced imaging systems and still allow them to connect to conventional electrical wall outlets that are most convenient for mobile applications, there is a need to provide additional electric power to augment power that can be drawn from the wall outlet. A fuel cell connected to the imaging device fulfills this need by augmenting electrical power that can be obtained from a typical electrical wall outlet.

A fuel cell for electrical power augmentation to an imaging system does not require recharging. Instead, the fuel cell uses an independent fuel source, such as a hydrocarbon, hydrogen, or other sources.

Although specific embodiments are illustrated and described herein, it will be appreciated by those of ordinary skill in the art that any arrangement which is calculated to achieve the same purpose may be substituted for the specific embodiments shown. This application is intended to cover any adaptations or variations. For example, although described in functional terms, one of ordinary skill in the art will appreciate that implementations can be made in any other convention that provides the required function.

In particular, one of skill in the art will readily appreciate that the names of the methods and apparatus are not intended to limit embodiments. Furthermore, additional methods and apparatus can be added to the components, functions can be rearranged among the components, and new components to correspond to future enhancements and physical devices used in embodiments can be introduced without departing from the scope of embodiments. One of skill in the art will readily recognize that embodiments are applicable to future fuel cell devices, different fuels, and new imaging systems.

The terminology used in this application is meant to include all imaging systems and environments and alternate technologies which provide the same functionality as described herein.

We claim:

1. An apparatus to image objects, the apparatus comprising:
    an imaging system;
    at least one fuel cell to provide electrical power augmentation to the imaging system;
    an exhaust receptacle operably coupled to the at least one fuel cell;
    a fuel tank operably coupled to the at least one fuel cell;
    a power module operably coupled to the imaging system and operable to be coupled to an electrical wall outlet;
    a power management system operably coupled via a control line to the power module; and
    a high voltage inverter directly coupled through a power line to the at least one fuel cell,
    wherein the power module does not include the at least one fuel cell.

2. The apparatus of claim 1, wherein the at least one fuel cell further comprises:
    a fuel cell operable to produce about 5 kW of electrical power.

3. The apparatus of claim 1, wherein the apparatus further comprises:
    a high voltage inverter operably coupled to the at least one fuel cell.

4. The apparatus of claim 1, further comprising an X-ray source operably coupled to the high voltage inverter.

5. The apparatus of claim 1, wherein the apparatus further comprises:
    the power module being operably coupled directly to the high voltage inverter and operable to be coupled directly to the electrical wall outlet.

6. The apparatus of claim 5, wherein the apparatus further comprises:
    the power management system being operably coupled to the high voltage inverter and operably coupled via a second control line to the at least one fuel cell.

7. The apparatus of claim 6, wherein the apparatus further comprises:
    the power management system operable to control power from the power module and the at least one fuel cell to the high voltage inverter.

8. The apparatus of claim 1, wherein the apparatus further comprises:
    a high voltage inverter operably coupled to the at least one fuel cell;
    the power module operably coupled to the high voltage inverter and operable to be coupled to an electrical wall outlet; and
    the power management system operably coupled to the high voltage inverter, operably coupled to the power module and operably coupled to the at least one fuel cell, the power management system operable to control power from the power module and the at least one fuel cell to the high voltage inverter.

9. The apparatus of claim 1, wherein the fuel tank further comprises:
    a fuel tank having a maximum capacity of between 1 gallons and 3 gallons.

10. The apparatus of claim 1, wherein the imaging system further comprises:
    a mobile imaging system.

11. The apparatus of claim 10, wherein the mobile imaging system further comprises:
    a mobile healthcare imaging system.

12. The apparatus of claim 11, wherein the mobile healthcare imaging system further comprises:
    a mobile healthcare X-ray imaging system.

13. A mobile X-ray imaging system comprising:
    a power management system;
    at least one fuel cell operably coupled to the power management system through a control line, wherein the control line causes the fuel cell to provide electrical power augmentation;
    an exhaust receptacle operably coupled to the at least one fuel cell;
    a fuel tank operably coupled to the at least one fuel cell;
    a high voltage inverter operably coupled to the at least one fuel cell through a power line and operably coupled to the power management system through a control line;
    an X-ray source operably coupled to the high voltage inverter through a power line, a power module operably coupled to the high voltage inverter and operable to be coupled to an electrical wall outlet; and wherein the power module does not include the at least one fuel cell.

14. The mobile X-ray imaging system of claim 13 further comprising:

the power management system operably coupled to the high voltage inverter, operably coupled to the power module and operably coupled to the at least one fuel cell, the power management system operable to control power from the power module and the at least one fuel cell to the high voltage inverter.

15. The mobile X-ray imaging system of claim 13 further comprising:

a power module operably coupled to the power management system through a control line, operably coupled to the high voltage inverter through a power line, and operable to be coupled to an electrical wall outlet.

16. The mobile X-ray imaging system of claim 13, wherein the at least one fuel cell further comprises:

a fuel cell operable to produce about 5 kW of electrical power.

17. The mobile X-ray imaging system of claim 13 further comprising:

a mobile X-ray healthcare imaging system.

18. A method performed by a power management system to control power in a mobile healthcare imaging system, the method comprising:

controlling power from at least one power module to a high voltage inverter, through at least one control line; and controlling power from at least one fuel cell to the high voltage inverter through at least one control line to provide electrical power augmentation to the mobile healthcare imaging system, wherein the at least one power module does not include the at least one fuel cell.

19. The method of claim 18, wherein the at least one fuel cell further comprises:

at least one fuel cell operable to produce about 5 kW of electrical power.

20. The method of claim 18, wherein the controlling power from the at least one power module and the controlling power from the at least one fuel cell is performed by executable instructions on a processor.

* * * * *